(12) United States Patent
Karam et al.

(10) Patent No.: US 9,086,483 B2
(45) Date of Patent: Jul. 21, 2015

(54) SYSTEMS AND METHODS FOR DETECTING AND/OR IDENTIFYING MATERIALS

(75) Inventors: Mostafa A. Karam, Moorpark, CA (US); A. Douglas Meyer, Woodland Hills, CA (US); Charles H. Volk, Newbury Park, CA (US); Raj K. Shori, North Hills, CA (US); Hector Macias, Newport Coast, CA (US)

(73) Assignee: NORTHROP GRUMMAN GUIDANCE AND ELECTRONICS COMPANY, INC., Woodland Hills, CA (US)

( * ) Notice: Subject to any disclaimer, the term of this patent is extended or adjusted under 35 U.S.C. 154(b) by 642 days.

(21) Appl. No.: 13/432,558

(22) Filed: Mar. 28, 2012

(65) Prior Publication Data

US 2012/0248313 A1    Oct. 4, 2012

Related U.S. Application Data (60) Provisional application No. 61/468,424, filed on Mar. 28, 2011, provisional application No. 61/476,542, filed on Apr. 18, 2011.

(51) Int. Cl.
*G01J 5/02* (2006.01)
*G01S 13/88* (2006.01)
(Continued)

(52) U.S. Cl.
CPC .......... *G01S 13/887* (2013.01); *G01N 21/3581* (2013.01); *G01J 5/10* (2013.01); *G01K 11/006* (2013.01); *G01N 21/3563* (2013.01)

(58) Field of Classification Search
CPC ... G01N 21/3581; G01V 8/005; G01S 13/887
USPC ...................................................... 250/341.1
See application file for complete search history.

(56) References Cited

U.S. PATENT DOCUMENTS 4,875,175 A    10/1989    Egee et al.
5,652,597 A    7/1997    Caille
(Continued)

FOREIGN PATENT DOCUMENTS

EP     0 967 459 A1    12/1999
WO    WO 99/28715    6/1999
WO    WO 2009115818 A2 *    9/2009

OTHER PUBLICATIONS

Chauveau et al., Determination of Resonance Poles of Radar Targets in Narrow Frequency Bands, Oct. 2007, Proceedings of the 4th European Radar Conference in Munich, Germany, pp. 122-125.*

(Continued)

*Primary Examiner* — David Porta
*Assistant Examiner* — Jeremy S Valentiner
(74) *Attorney, Agent, or Firm* — Tarolli, Sundheim, Covell & Tummino (57) ABSTRACT

One embodiment of the invention includes a material detection system. The system includes a sensor system configured to collect radiation from a region of interest. The collected radiation can include a plurality of frequency bands. The system also includes a processing unit configured to detect a material of interest. The material of interest can be a concealed dielectric material, and the processing unit can be configured to decompose the collected radiation into natural resonance signals to analyze the natural resonance signals to detect an anomaly corresponding to the concealed dielectric material based on wave characteristics of the natural resonance signals. The processing unit could also include processing layers associated with the plurality of frequency bands for detecting and identifying the material of interest based on wave characteristics associated with each of the plurality of frequency bands of the collected radiation.

21 Claims, 8 Drawing Sheets

(51) Int. Cl.
*G01N 21/3581* (2014.01)
*G01J 5/10* (2006.01)
*G01K 11/00* (2006.01)
*G01N 21/3563* (2014.01)

(56) References Cited

U.S. PATENT DOCUMENTS

| | | | |
|---|---|---|---|
| 5,757,496 A | 5/1998 | Yamazaki | |
| 5,942,899 A * | 8/1999 | Shrekenhamer et al. | 324/326 |
| 6,545,763 B1 | 4/2003 | Kim et al. | |
| 6,777,684 B1 | 8/2004 | Volkov et al. | |
| 6,850,543 B2 | 2/2005 | Cundiff et al. | |
| 7,155,363 B1 * | 12/2006 | Rosenthal et al. | 702/135 |
| 7,280,078 B2 | 10/2007 | Salsman et al. | |
| 7,306,367 B2 | 12/2007 | Salem et al. | |
| 7,339,682 B2 | 3/2008 | Aiyer et al. | |
| 7,471,392 B2 | 12/2008 | Norton et al. | |
| 7,489,391 B2 | 2/2009 | Engheta et al. | |
| 7,515,347 B2 | 4/2009 | Hauschild et al. | |
| 7,616,323 B2 | 11/2009 | DeLega et al. | |
| 7,687,773 B2 | 3/2010 | Siegel et al. | |
| 2003/0163042 A1 | 8/2003 | Salmon | |
| 2004/0065831 A1 * | 4/2004 | Federici et al. | 250/341.1 |
| 2004/0136041 A1 | 7/2004 | Togino | |
| 2006/0273255 A1 * | 12/2006 | Volkov et al. | 250/336.1 |
| 2007/0014319 A1 | 1/2007 | Hill et al. | |
| 2008/0074674 A1 | 3/2008 | Chen et al. | |
| 2008/0306719 A1 | 12/2008 | Freier | |
| 2009/0319225 A1 * | 12/2009 | Mansfield | 702/170 |
| 2010/0007863 A1 | 1/2010 | Jordanoska | |
| 2011/0004091 A1 | 1/2011 | Brooks et al. | |
| 2011/0102235 A1 * | 5/2011 | Abdillah et al. | 342/22 |
| 2011/0181300 A1 * | 7/2011 | Bowring et al. | 324/637 |

OTHER PUBLICATIONS

Braslaysky, Glossary of Terms Used in Photochemistry 3rd Edition, 2007, Pure App. Chem., vol. 79 No. 3, pp. 293 & 324.*

Co-Pending Application Entitled: "*System and Methods for Detecting and/or Identifying Materials Based on Electromagnetic Radiation*", (attached herewith).

* cited by examiner

SYSTEMS AND METHODS FOR DETECTING AND/OR IDENTIFYING MATERIALS

RELATED APPLICATIONS

The present invention claims priority from U.S. Provisional Application Ser. No. 61/468,424, filed 28 Mar. 2011 and U.S. Provisional Application Ser. No. 61/476,542, filed 18 Apr. 2011, both of which are herein incorporated by reference in their entirety.

TECHNICAL FIELD

The present invention relates generally to sensor systems, and specifically to systems and methods for detecting and/or identifying materials.

BACKGROUND

There has been an ever increasing demand in security, warfare, and peacekeeping applications for a manner to accurately detect the presence of dangerous materials, such as concealed weapons, chemicals, or explosives. In the case of concealed explosives or chemicals, it is typically necessary to detect the materials from a suitable standoff distance, so as to avoid danger to the individuals that attempt to detect the concealed materials. Furthermore, it may be desirable to identify the specific type of materials, such as to determine a source of the dangerous materials or to assess the potential for damage or harm resulting from detonation or release of the dangerous materials.

There are many techniques that have been efficiently used in detecting whether certain dielectric materials, such as chemicals or explosives, are present and/or in identifying the type of dielectric material. For example, typical detection/identification systems include cavity resonators, spectroscopes, time domain reflectors, and a variety of other techniques. However, most such techniques are either laboratory based techniques or contact techniques. As a result, the techniques are unable to be used in the context of a field operation or at a large public event (LPE) where farther standoff distances are required. In addition, certain detection techniques are unable to penetrate intervening materials, such as clothing and/or precipitation or atmospheric conditions.

SUMMARY

One embodiment of the invention includes a material detection system. The system includes a sensor system configured to collect radiation from a region of interest. The system also includes a processing unit configured to decompose the collected radiation into natural resonance signals and to analyze the natural resonance signals to detect an anomaly corresponding to a concealed dielectric material based on wave characteristics of the natural resonance signals.

Another embodiment of the invention includes a method for detecting and identifying a concealed dielectric material in a region of interest. The method includes collecting radiation from the region of interest and decomposing the collected radiation into natural resonance signals. The method also includes detecting an anomaly corresponding to the concealed dielectric material in the natural resonance signals associated with the region of interest. The method further includes identifying the concealed dielectric material in response to detecting the anomaly based on wave characteristics associated with the natural resonance signals and the collected radiation.

Another embodiment of the invention includes a material detection system. The system includes a sensor system configured to collect radiation comprising a plurality of frequency bands from a region of interest. The system also includes a processing unit comprising a first processing layer associated with a first frequency band of the plurality of frequency bands of the radiation and a second processing layer associated with a second frequency band of the plurality of frequency bands of the radiation. The first processing layer can be configured to detect a material of interest in the region of interest based on wave characteristics associated with the first frequency band and the second processing layer being configured to identify the material of interest based on wave characteristics associated with the second frequency band.

Another embodiment of the invention includes a method for detecting and identifying a material in a region of interest. The method includes determining a scene physical temperature associated with the region of interest, and collecting first wavelength radiation from the region of interest. The method also includes detecting the presence of the material in the region of interest based on the scene physical temperature and wave characteristics associated with the collected first wavelength radiation and collecting second wavelength radiation from the region of interest in response to detecting the presence of the material. The method further includes identifying the material based on the scene physical temperature and wave characteristics associated with the collected second wavelength radiation.

DETAILED DESCRIPTION

The present invention relates generally to sensor systems, and specifically to systems and methods for detecting and/or identifying materials. A detection and identification system can include a sensor system and a processing unit. The sensor system can be configured to collect radiation from a region of interest. The radiation can include one or more types of radiation, such as millimeter-wave (MMW), terahertz (THz), and/or infrared (IR) radiation from the region of interest. The sensor system can be configured as a passive radiometer, or can be configured as an active sensor, such as a backscattering or a bi-static scatterometer/radar. Thus, the sensor system can be configured to gather wave-characteristic information regarding the region of interest. For example, the collected orthogonally-polarized radiation can be decomposed into natural resonance signals, with the natural resonance signals or the radiation itself being processed by an algorithm to ascertain reflectivity data of the material.

For example, the sensor system can be configured to collect IR radiation from the region of interest to obtain a physical temperature of the region of interest. A physical temperature of the region of interest can thus be ascertained. The sensor system can also collect radiation of the region of interest, such as orthogonally-polarized radiation, to obtain signal characteristics of the region of interest, such as to detect the presence of an anomaly that can correspond to a dielectric material. As provided herein, the term "dielectric material" can be used to describe dangerous materials, such as concealed weapons, chemicals, and/or explosives. As another example, the sensor system can also be configured to collect radiation of a different wavelength to ascertain a refractive index of the material, such as to identify a specific type of material (e.g., in response to detecting the anomaly). The processing unit can be configured to implement one or more signal processing algorithms that can detect the presence of the dangerous dielectric material in the region of interest and/or to identify the specific type of dangerous dielectric material.

Figure 1:
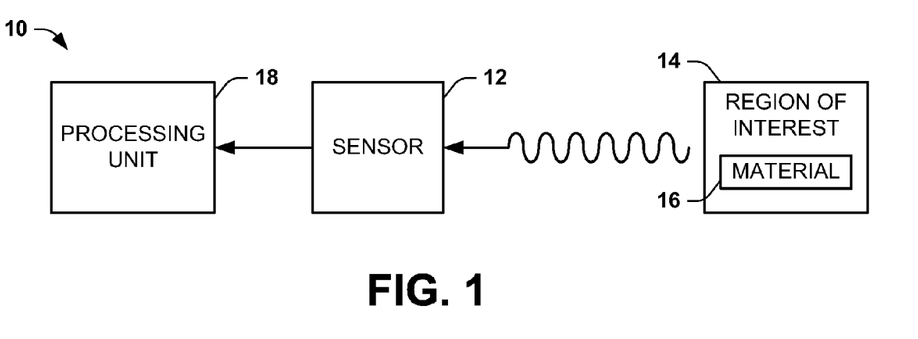
FIG. 1 illustrates an example of a material detection system in accordance with an aspect of the invention.

FIG. 1 illustrates an example of a material detection system 10 in accordance with an aspect of the invention. The material detection system 10 can be implemented in a variety of applications to detect and/or to identify potentially dangerous dielectric materials, such as explosives and/or chemicals. For example, the material detection system 10 can be implemented to scan people in a crowd in a non-invasive manner to detect the presence of concealed weapons, explosives, or improvised explosive devices (IEDs), to scan large public venue for explosive devices, and/or to scan a region of interest for buried explosives and/or road-side bombs. Thus, the material detection system 10 can be implemented in a variety of applications.

The material detection system 10 includes a sensor 12 that is configured to collect radiation from a region of interest 14. The sensor 12 can be configured to collect the radiation at one or more frequency bands, such as including one or more of millimeter-wave (MMW), terahertz (THz), and infrared (IR) radiation. The sensor 12 can be configured as a passive radiometer, or can be an active sensor, such as a scatterometer (e.g., backscattering or bi-static scatterometer/radar). The sensor 12 can thus acquire wave characteristics to detect the presence of a material 16. As an example, the material 16 can be a dangerous material, such as an explosive or hazardous chemical, or can be a weapon. Thus, the region of interest 14 can correspond to a crowd of people, a large public venue, or a geographical area in which the material 16 is concealed or is otherwise obscured from close proximal view.

The sensor 12 provides input in the form of wave data to a processing unit 18. The processing unit 18 can thus be configured to process the wave data to implement detection of and/or possible identification of the material 16. For example, the processing unit 18 can be configured to implement an algorithm based on emissivity, brightness temperature, or a variety of other received wave characteristics of the region of interest 14 to detect an anomaly that could correspond to the presence of the material 16. The processing unit 18 could then implement the algorithm to confirm the presence of the material 16, or could further process the anomaly to determine the specific identity of the material 16. For example, the processing unit 18 could be configured to determine a dielectric constant of the material 16, such as based on natural resonance signals and observation angle of the sensor 12 relative to the region of interest 14, in a non-imaging manner. The processing unit 18 could thus identify the specific material 16 based on the calculated refractive index.

As one example, the material detection system 10 in the example of FIG. 1 can be configured to implement natural resonance signals of the region of interest 14 to determine the presence and/or identity of the material 16. Concealed explosives, similar to any other buried targets, have a complex natural resonance that depends on dielectric and geometric characteristics of the concealed explosives and a host media. In the frequency domain f, the complex natural resonance representation for a noisy data set y(f) acquired over a concealed explosive could be written as follows:

$$y(f) = \sum_{m=0}^{M} A_m \exp(\varpi_m f) + n(f)$$ Equation 1

$$\varpi_m = -\kappa_m \pm 2\pi j T_m$$ Equation 2

$$A_m = |A_m| \exp(j\phi_m)$$ Equation 3

Where:
$A_m$ terms correspond to residues;
$\varpi_m$ terms correspond to poles;
$\kappa_m$ terms correspond to damping rates;
$T_m$ terms correspond to resonance periods; and
n(f) corresponds to noise.

A similar representation to Equations 1-3 could be written for data acquired in the time domain t with replacing the resonance period $T_m$ by the resonance frequency $f_m$ and replacing the frequency f by time t.

Figure 2:
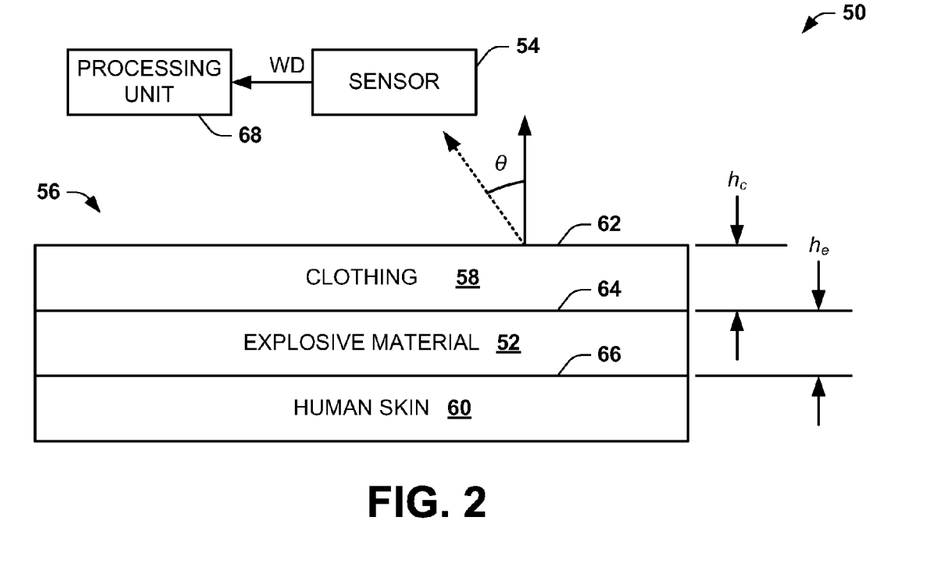
FIG. 2 illustrates an example diagram for detecting an explosive material in accordance with an aspect of the invention.

FIG. 2 illustrates an example of a material detection system 50 in accordance with an aspect of the invention. The material detection system 50 can correspond to the material detection system 10 of the example of FIG. 1 that implements natural resonance signals to detect and/or identify the material 16 within the region of interest 14. The material detection system 50 can be configured to detect a concealed explosive material 52, which can correspond to the material 16 in the example of FIG. 1. Therefore, reference is to be made to the example of FIG. 2 in the following description of the example of FIG. 1.

In the example of FIG. 2, a sensor 54 is demonstrated as receiving radiation from a region of interest 56. The region of interest 56 is demonstrated as a layer of cloth 58 at an exterior and the explosive material 52 between the layer of cloth 58 and human skin 60. An interface between air and the cloth layer 58 is demonstrated at 62, an interface between the cloth layer 58 and the explosive material 52 is demonstrated at 64, and an interface between the explosive material 52 and the human skin 60 is demonstrated at 66. Therefore, the material detection system 10 is implemented in the example of FIG. 2 to detect the explosive material 52 as concealed on a person, such that the region of interest 14 can be the given person or a crowd of people that includes the person concealing the explosive material 52. As an example, the sensor 54 can encompass a wideband THz sensor operating within one of the atmospheric windows at the frequency band of approximately 0.1-1 THz. The frequency band of the sensor 54 can be selected depending on the operating environment of the sensor 54.

As an example, the sensor 54 may be an active THz sensor (i.e., a radar sensor) or a passive THz sensor (i.e., a radiometer sensor). For example, the sensor 54 can be implemented as a dual polarized passive sensor operating within the frequency band of approximately 0.62-0.72 THz. As another example, the sensor 54 can be implemented as an active THz sensor operating at a frequency of around 0.22 THz to substantially mitigate the effect of the scattered radiation being localized around the reflection specular directions. Thus, in the example of the sensor 54 being an active sensor, the sensor 54 can be configured as one of a bi-static radar system or a backscattered radar system operating at a substantially normal angle of incidence. However, it is to be understood that the sensor 54 is not limited to these examples, but that other types of sensors operating at other frequency ranges can be implemented for detection and/or identification of the explosive material 52. In the example of FIG. 2, the sensor 54 provides a signal WD corresponding to the wave characteristics of the collected radiation to a processing unit 68.

In the example of FIG. 2, a p (p=v, h) polarized brightness temperature $T_p(\theta)$ can be measured by the sensor 54 (e.g., configured as a THz radiometer) at an observation angle $\theta$. The brightness temperature $T_p(\theta)$ could be written as follows:

$$T_p(\theta) = (1 - R_p(\theta))T + R_p(\theta)T_{sky}(\theta) \quad \text{Equation 4}$$

Where:
T is a scene physical temperature;
$T_{sky}(\theta)$ is a sky brightness temperature; and
$R_p(\theta)$ is a scene reflectivity.

The scene physical temperature T can be obtained in a number of different ways. For example, the sensor 54 can incorporate a thermal IR radiometer operating in a wavelength band of approximately 4-12 μm. As another example, the sky brightness temperature $T_{sky}(\theta)$ can be obtained from meterological data. Upon obtaining the scene physical temperature T and the sky brightness temperature $T_{sky}(\theta)$, the scene reflectivity $R_p(\theta)$ can be obtained as follows:

$$R_p(\theta) = \frac{T - T_p(\theta)}{T - T_{sky}(\theta)}. \quad \text{Equation 5}$$

Figure 3:
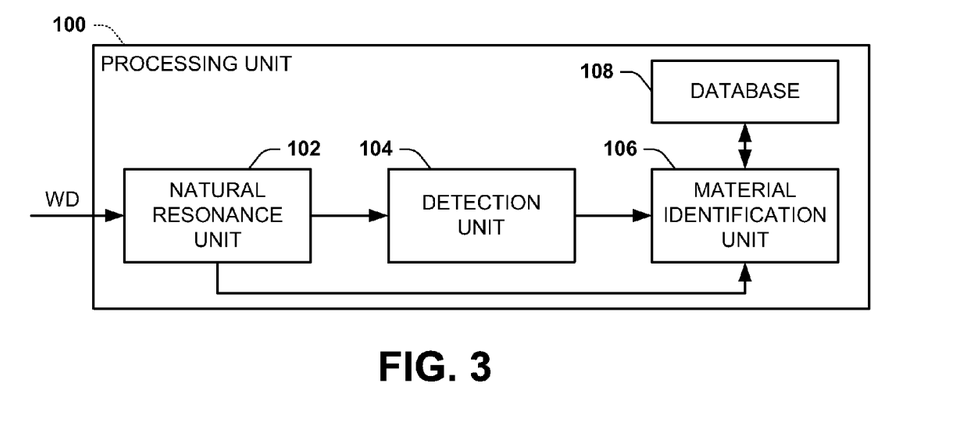
FIG. 3 illustrates an example of a processing unit in accordance with an aspect of the invention.

FIG. 3 illustrates an example of a processing unit 100 in accordance with an aspect of the invention. The processing unit 100 can correspond to the processing unit 18 in the example of FIG. 1 for the material detection system 10 that implements natural resonance signals to detect and/or identify the explosive material 52 (i.e., implementing the sensor 54 in the example of FIG. 2). Therefore, reference is to be made to the examples of FIGS. 1 and 2 in the following description of the example of FIG. 3.

The processing unit 100 includes a natural resonance unit 102 that receives the signal WD from the sensor 54. The natural resonance unit 102 can be configured to decompose the scene reflectivity data $R_p(\theta)$ into the natural resonance signals of Equations 1-3. To achieve such a process, the natural resonance unit 102 can employ any of a variety of signal processing techniques, such as the total square matrix pencil method (TLS-MPM) or a variety of other methods (e.g., Prony's Method).

Figure 4:
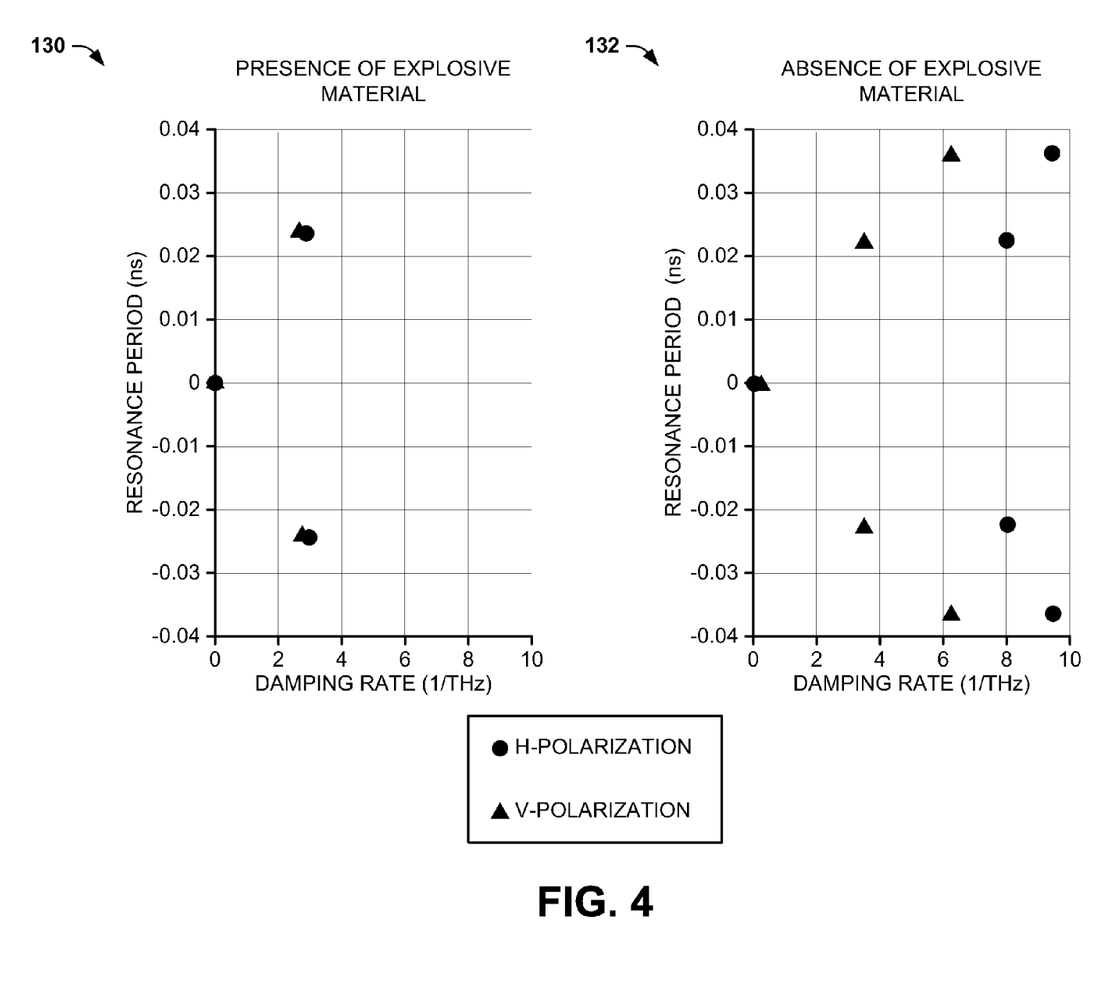
FIG. 4 illustrates an example of graphs depicting natural resonance poles in accordance with an aspect of the invention.
Figure 5:
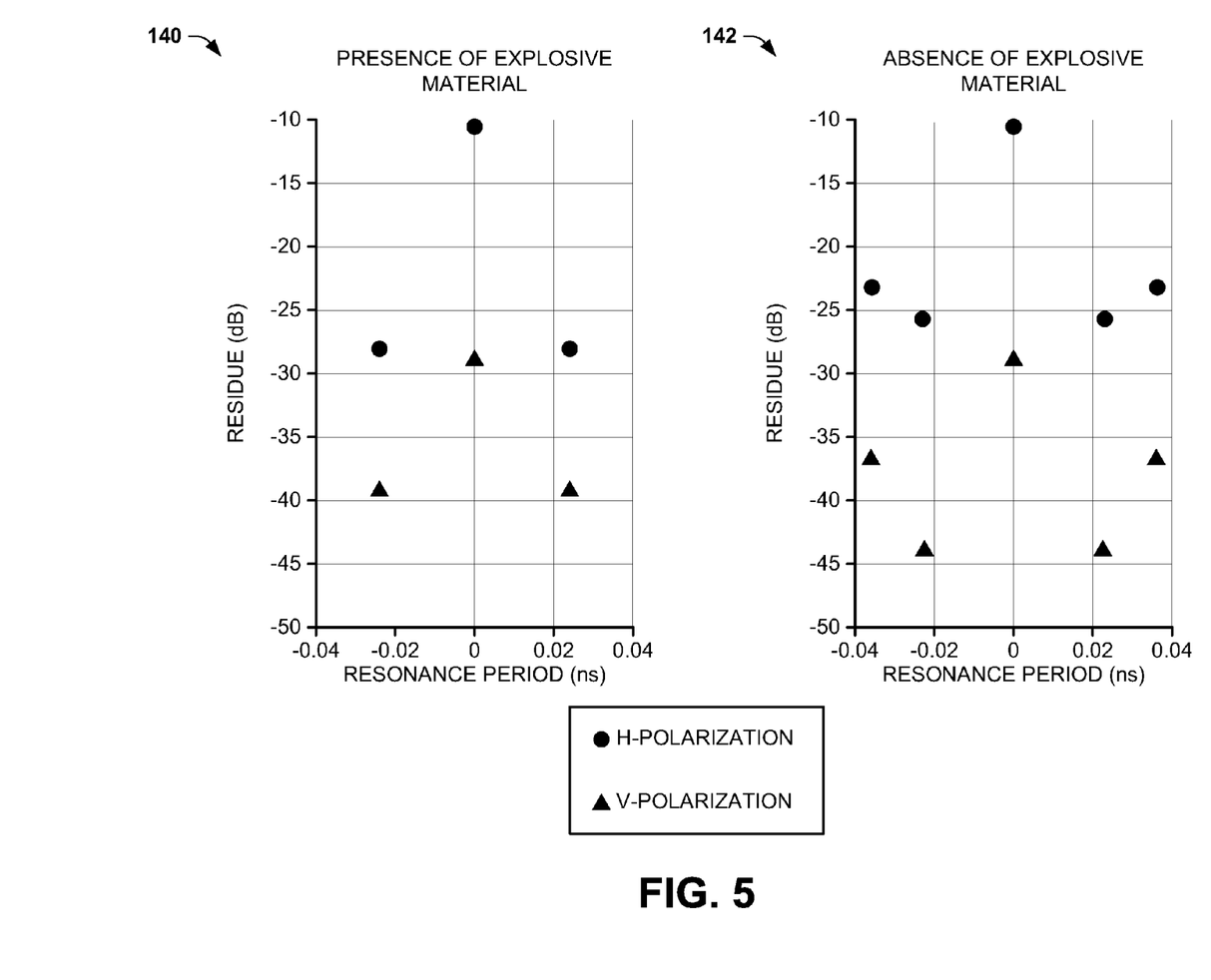
FIG. 5 illustrates an example of graphs depicting natural resonance residues in accordance with an aspect of the invention.

FIG. 4 illustrates an example of graphs 130 and 132 depicting natural resonance poles, and FIG. 5 illustrates an example of graphs 140 and 142 depicting natural resonance residues in accordance with an aspect of the invention. Specifically, the examples of FIGS. 4 and 5 demonstrate application of the TLS-MPM on simulated THz radiometer data in the presence of a concealed C-4 explosive, as demonstrated in respective graphs 130 and 140, and in the absence of any explosive, as demonstrated in respective graphs 132 and 142. The simulated data is generated for two polarizations: horizontal polarization (H Pol), demonstrated as circles, and vertical polarization (V Pol), demonstrated as triangles. The simulated data is generated based on an observation angle $\theta$ of 50°, as demonstrated in the example of FIG. 2. The cloth layer 58 is taken to have dielectric constant of approximately 1.9586–j0.1042 and a depth $h_c$ of approximately 3 mm. The explosive material 52 is taken to have a known dielectric constant and a depth $h_e$ of approximately 5 mm. The human skin 60 located below the explosive material 52 is taken to have a known dielectric constant. Furthermore, in the examples of FIGS. 4 and 5, in the absence of the explosive material 52, a void between the cloth layer 58 and the human skin 60 is taken to have a depth of approximately 3 mm. The graphs 130, 132, 140, and 142 in the respective examples of FIGS. 4 and 5 thus indicate that both poles and residues have either real or complex values. When complex values occur, they typically occur in pairs, with elements of each pair being conjugate with respect to each other.

Referring back to the example of FIG. 3, after obtaining the poles and residues, the natural resonance unit 102 provides them to a detection unit 104. The detection unit 104 is configured to count the number of poles occurring within a specified length of the damping factor axis, such as demonstrated in the graphs 130, 132, 140, and 142 in the examples of FIGS. 4 and 5, starting from the origin. Upon determining a relatively fewer number of poles, the detection unit 104 can identify the presence of an anomaly. The anomaly could thus correspond to an explosive material (e.g., the explosive material 52). Otherwise, the detection unit 104 acknowledges the absence of an explosive material 52, such that the sensor 54 and the natural resonance unit 102 can continue to acquire radiation and corresponding natural resonance signal data from the region of interest 14.

The detection unit 104 can select the number of poles as criteria for confirming the presence of an anomaly based on the three leading terms in the series expansion of the reflectivity $R_p(\theta)$ of a concealed anomaly/explosive, as follows:

$$R_p(\theta) = |r_{pc}(\theta)|^2 + |1 - r_{pc}^2(\theta)|^2 |r_{pe}(\theta)|^2 \exp(-\alpha_c(\theta)h_c) + \quad \text{Equation 6}$$
$$r_{pc}(\theta)(1 - r_{pc}^2(\theta)^* r_{pe}^*(\theta) \exp(2j\gamma_c^* h_c) +$$
$$r_{pc}^*(\theta)(1 - r_{pc}^2(\theta))r_{pe}(\theta) \exp(-2j\gamma_c h_c) +$$
$$r_{pc}(\theta)(1 - r_{pc}^2(\theta))^* (1 - r_{pe}^2(\theta))^* r_{ps}^*(\theta) \exp(2j(\gamma_c^* h_c +$$
$$\gamma_e^* h_e)) + r_{pc}^*(\theta)(1 - r_{pc}^2(\theta))(1 -$$
$$r_{pe}^2(\theta))r_{ps}(\theta) \exp(-2j(\gamma_c h_c + \gamma_e h_e)) + \ldots$$

Where:
"*" terms correspond to the complex conjugate operators;
$r_{pc}(\theta)$, $r_{pe}(\theta)$, and $r_{ps}(\theta)$ are p (p=v, h) polarized Fresnel reflection coefficients at the air-cloth interface 62, cloth-explosive interface 64, and explosive-skin interface 66, respectively; and
$\gamma_c(\theta)$ and $\gamma_e(\theta)$ are propagation constants within the cloth layer 58 and the anomaly explosive material 52.

$$\gamma_c(\theta) = \beta_c(\theta) - j\alpha_c(\theta) = (2\pi f/c)\sqrt{\epsilon_c - \sin^2\theta} \quad \text{Equation 7}$$

$$\gamma_e(\theta) = \beta_e(\theta) - j\alpha_e(\theta) = (2\pi f/c)\sqrt{\epsilon_e - \sin^2\theta} \quad \text{Equation 8}$$

Where:

c is the speed of light in vacuum;

$\in_c$ is the relative dielectric constant of the cloth layer 58; and $\in_e$ is the relative dielectric constant of the human skin 60.

Comparing Equation 6 with Equation 2, mathematical expressions for the first five poles can be written as:

$$\bar{\omega}_{0p}=0$$

$$\bar{\omega}_{1p}=-2jh_c(2\pi/c)\sqrt{\in_c-\sin^2\theta}$$

$$\bar{\omega}_{2p}=2jh_c(2\pi/c)\sqrt{\in_c^*-\sin^2\theta}$$

$$\bar{\omega}_{3p}=-2j(2\pi/c)(h_c\sqrt{\in_c-\sin^2\theta}+h_e\sqrt{\in_e-\sin^2\theta})$$

$$\bar{\omega}_{4p}=2j(2\pi/c)(h_c\sqrt{\in_c^*-\sin^2\theta}+h_e\sqrt{\in_e^*-\sin^2\theta}) \quad \text{Equations 9}$$

Comparing Equation 6 against Equation 3, the mathematical formulations of the first five residues can be written as:

$$A_{0p}=|r_{pc}(\theta)|^2$$

$$A_{1p}=r_{pc}(\theta)(1-r_{pc}^2(\theta))^*r_{pe}^*(\theta)$$

$$A_{2p}=r_{pc}^*(\theta)(1-r_{pc}^2(\theta))r_{pe}(\theta)$$

$$A_{3p}=r_{pc}(\theta)(1-r_{pc}^2(\theta))^*(1-r_{pe}^2(\theta))^*r_{ps}^*(\theta)$$

$$A_{4p}=r_{pc}^*(\theta)(1-r_{pc}^2(\theta))(1-r_{pe}^2(\theta))r_{ps}(\theta) \quad \text{Equations 10}$$

From Equations 9 and Equations 10, it is demonstrated that the poles and residues of zero order ($\bar{\omega}_0$, $A_{0p}$) are associated with Fresnel reflection at the air-cloth layer interface 62. Therefore, the zero order residues $A_{0p}$ are the same either in the presence of or in the absence of the explosive material 52, as demonstrated in the example of FIG. 4. The first and second order poles ($\bar{\omega}_{1p}$, $\bar{\omega}_{2p}$) and residues ($A_{1p}$, $A_{2p}$) are thus associated with reflection from the explosive material 52 based on attenuation by the cloth layer 58. The third and fourth order poles ($\bar{\omega}_{3p}$, $\bar{\omega}_{4p}$) and residues ($A_{3p}$, $A_{4p}$) are similarly thus associated with reflection from the human skin 60 based on attenuation by both the cloth layer 58 and the explosive material 52. Accordingly, such third and fourth order poles ($\bar{\omega}_{3p}$, $\bar{\omega}_{4p}$) and residues ($A_{3p}$, $A_{4p}$) disappear in the presence of the explosive material due to the higher attenuation rates within the explosive material 52. In the absence of the explosive material 52, the attenuation rates are very low, and the third and fourth order poles ($\bar{\omega}_{3p}$, $\bar{\omega}_{4p}$) and residues ($A_{3p}$, $A_{4p}$), as well as their counterparts of higher orders, contribute to the data acquired by the detection unit 104.

The data acquired by the detection unit 104 is provided to a material identification unit 106. The material identification unit 106 can be configured to extract the observation angle $\bar{\theta}$, the cloth layer depth $\bar{h}_c$, the cloth layer dielectric constant $\bar{\in}_c$, and the Fresnel reflection coefficients $\bar{r}_{hc}(\theta)$, $\bar{r}_{vc}(\theta)$ at the air-cloth layer interface 62 based on values of the zero order residue ($A_{0p}$) and the first and the second order poles ($\bar{\omega}_{1p}$, $\bar{\omega}_{2p}$). Upon obtaining such parameters, the material detection unit 106 can implement the parameters along with either the first or second order residues ($A_{1p}$, $A_{2p}$) in obtaining the complex dielectric constant $\bar{\in}_e$ of the detected anomaly. The complex dielectric constant $\bar{\in}_e$ can then be compared against dielectric constants of known explosives, such as stored in a database 108, to identify the explosive type.

The material identification unit 106 can extract the observation angle $\bar{\theta}$ by using the following identity:

$$\bar{\theta}=\cos^{-1}\left\{\left[1+\vartheta\left(v_{hv}-\sqrt{v_{hv}^2-(1+\zeta^2)}\right)\right]^{-0.5}\right\} \quad \text{Equation 11}$$

Where:

$$\vartheta = \frac{1}{v_h-\sqrt{v_h^2-(1+\zeta^2)}} \quad \text{Equations 12}$$

$$\zeta = \frac{\kappa_1}{2\pi T_1}$$

$$v_{hv} = \frac{A_{0h}+A_{0v}}{A_{0h}-A_{0v}}$$

$$v_h = \frac{1+A_{0h}}{1-A_{0h}}$$

Where: $\kappa_1$ and $T_1$ are the attenuation rate and the resonance period, respectively, of the first order pole of Equation 2; and $A_{0h}$ and $A_{0v}$ are the zero order residues of the horizontal and vertical polarization, respectively.

It is to be understood that, as described herein, variables that include a bar correspond to extracted quantities to distinguish them from measured quantities and from the quantities defining the natural resonance signals (i.e., values of the poles and the zeros). The extracted value of the observation angle $\bar{\theta}$ is used in extracting the depth $h_c$ of the cloth layer 58, as follows:

$$\bar{h}_c = \frac{cT_1}{2\vartheta\cos\bar{\theta}} \quad \text{Equation 13}$$

After extracting the values for the observation angle $\bar{\theta}$ and the depth $\bar{h}_c$ of the cloth layer 58, the material identification unit 106 can extract the complex value of the cloth layer 58 relative dielectric constant $\bar{\in}_c$ as follows:

$$\bar{\in}_c = \bar{\in}_c' - j\bar{\in}_c'', \quad \text{Equation 14}$$

Values of the two components of the dielectric constant of the cloth layer 58 could be estimated as follows.

$$\bar{\varepsilon}_c' = \sin^2\bar{\theta} + \left(\frac{c}{2\bar{h}_c}\right)^2\left[T_1^2-\left(\frac{\kappa_1}{2\pi}\right)^2\right] \quad \text{Equations 15}$$

$$\bar{\varepsilon}_c'' = \left(\frac{c}{2\bar{h}_c}\right)^2\left[\frac{\kappa_1 T_1}{\pi}\right]$$

Extracting the values of the dielectric constant of the cloth layer 58 and the observation angle $\bar{\theta}$ thus enables the material identification unit 106 to construct the Fresnel reflection coefficients $\bar{r}_{hc}(\theta)$, $\bar{r}_{vc}(\theta)$ embedded in the formulations of the first and second order residues of Equations 10. Specifically, the values of the horizontal and vertical Fresnel reflection coefficients $\bar{r}_{hc}(\theta)$ $\bar{r}_{vc}(\theta)$ at the air-cloth interface 62 could be obtained as follows:

$$\bar{r}_{hc}(\theta) = \frac{\cos\bar{\theta}-\sqrt{\bar{\varepsilon}_c-\sin^2\bar{\theta}}}{\cos\bar{\theta}+\sqrt{\bar{\varepsilon}_c-\sin^2\bar{\theta}}} \quad \text{Equations 16}$$

-continued $$\bar{r}_{vc}(\theta) = \bar{r}_{hc}(\theta)\left[\frac{\cos\theta\sqrt{\bar{\varepsilon}_c - \sin^2\theta} - \sin^2\theta}{\cos\theta\sqrt{\bar{\varepsilon}_c - \sin^2\theta} - \sin^2\theta}\right]$$

The extracted values of the Fresnel reflection coefficients $\bar{r}_{hc}(\theta)$, $\bar{r}_{vc}(\theta)$ at the air-cloth interface 62, as calculated in Equations 16, are then incorporated with the first order residues to extract values of the horizontal and vertical Fresnel reflection coefficients $\bar{r}_{hc}(\theta)$, $\bar{r}_{vc}(\theta)$ at the cloth-explosive layer interface 64. In achieving this process the apparatus exploits these two identities.

$$\bar{r}_{he}(\theta) = \frac{A_{2h}}{\bar{r}^*_{hc}(\theta)[1 - \bar{r}^2_{he}(\theta)]}$$
$$\bar{r}_{ve}(\theta) = \frac{A_{2v}}{\bar{r}^*_{vc}(\theta)[1 - \bar{r}^2_{ve}(\theta)]}$$

Equations 17

Upon obtaining the values of the Fresnel reflection coefficients $\bar{r}_{he}(\theta)$, $\bar{r}_{ve}(\theta)$ at the cloth-explosive interface 64, they are inverted to extract the complex value of the explosive dielectric constant $\overline{\mathbb{E}}_e$:

$$\overline{\mathbb{E}}_e = \overline{\mathbb{E}}_e' - j\overline{\mathbb{E}}_e''$$

Equation 18

Values of the real $\overline{\mathbb{E}}_e'$ and imaginary $\overline{\mathbb{E}}_e''$ of the explosive dielectric constant can be estimated as follows:

$$\varepsilon_e' = \sin^2\theta + \text{Re}\left\{\frac{\sin^4\theta}{[\bar{\varepsilon}_c - \sin^2\theta]}\left[\frac{\bar{r}_{he}(\theta) - \bar{r}_{ve}(\theta)}{\bar{r}_{he}(\theta) + \bar{r}_{ve}(\theta)}\right]^2\right\}$$
$$e_e'' = \text{Im}\left\{\frac{\sin^4\theta}{[\bar{\varepsilon}_c - \sin^2\theta]}\left[\frac{\bar{r}_{he}(\theta) - \bar{r}_{ve}(\theta)}{\bar{r}_{he}(\theta) + \bar{r}_{ve}(\theta)}\right]^2\right\}$$

Equations 19

Where: Re{ }, and Im{ } are the real and imaginary part operators.

After extracting the complex value of the anomaly dielectric constant based on Equations 18 and 19, the material identification unit 106 can identify the anomaly corresponding to the explosive material 52. This can be achieved through comparing the dielectric constant value $\overline{\mathbb{E}}_e$ against dielectric constants of known explosives stored in the database 108. If the dielectric constant value $\overline{\mathbb{E}}_e$ matches a value within the database 108, the material identification unit 106 can display the name of the explosive material 52 associated with that value. Otherwise the material identification unit 106 can display that the anomaly corresponding to the explosive material 52 is unknown.

Accordingly, the examples of FIGS. 2-5 demonstrate a manner in which a concealed and potentially dangerous material, such as an explosive, can be detected and/or identified based on using a sensor that implements multiple wavelengths. Specifically, the sensor 54 is implemented to obtain a scene reflectivity, from which poles and residues can be ascertained based on natural resonance signals. An algorithm can thus be implemented to determine a dielectric constant of a concealed material based on the poles and residues, from which the concealed material can be identified. As a result, the material detection system 50 can be used in a variety of security, military, and/or peacekeeping applications for detecting and identifying explosives from sufficiently safe standoff distances.

Figure 6:
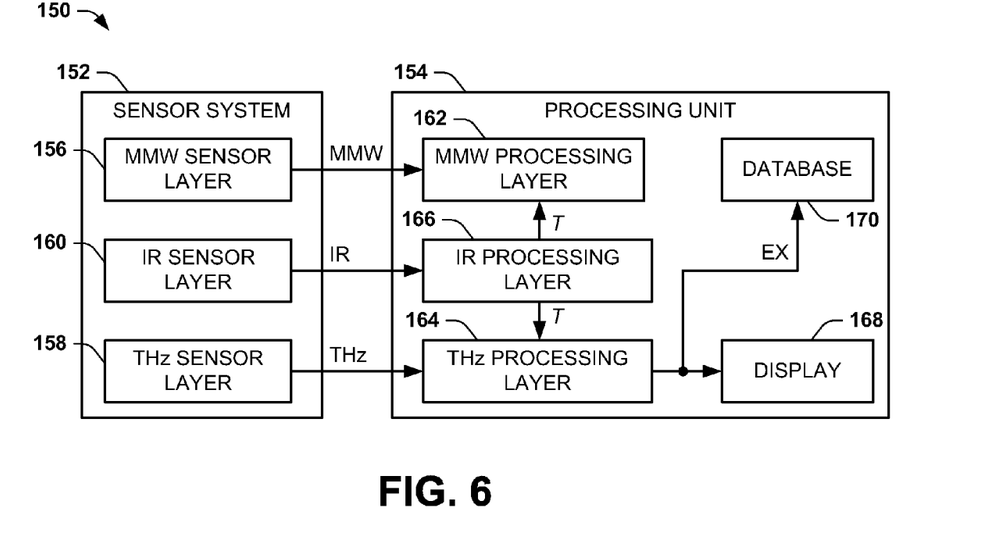
FIG. 6 illustrates another example of a material detection system in accordance with an aspect of the invention.

As another example, the material detection system 10 in the example of FIG. 1 can be configured to implement collection of three layers of radiation of the region of interest 14 from three respective sensor layers associated with the sensor 12 to determine the presence of and identity of the material 16 based on a refractive index of the material. FIG. 6 illustrates another example of a material detection system 50 in accordance with an aspect of the invention. The material detection system 50 can correspond to the material detection system 10 in the example of FIG. 1, and thus, reference is to be made to the example of FIG. 1 in the following description of the example of FIG. 6.

The material detection system 150 includes a sensor system 152 and a processing unit 154. The sensor system 152 includes a millimeter-wave (MMW) sensor layer 156, a terahertz (THz) sensor layer 158, and an infrared (IR) sensor layer 160 that can include one or more IR sensors. As an example, the sensory system 152 can correspond to the sensor 12 in the example of FIG. 1. The MMW sensor layer 156 can be configured to detect the presence of the material 16, such as may be an explosive. The MMW sensor layer 156 can be selected to operate in a frequency that is sufficient for operation in substantially any weather conditions and at any time of day, and also exhibits sufficient penetration capability. The THz sensor layer 158 can be configured to identify the material 16, such as by identifying the explosive type, and can also detect fine structures therein, such as wires of an associated bomb. The THz sensor layer 158 can operate at a single frequency within one of the THz atmospheric transmission windows, such as around 0.22 THz or around 0.65 THz. The IR sensor layer 160 can be configured to ascertain a scene physical temperature.

The processing unit 154 includes an MMW processing layer 162, a THz processing layer 164, and an IR processing layer 166. The MMW sensor layer 156 collects MMW radiation from the region of interest 14 and provides a signal MMW associated with MMW wave characteristics of the region of interest 14 to the MMW processing layer 162. Similarly, the THz sensor layer 158 collects THz radiation from the region of interest 14 and provides a signal THz associated with THz wave characteristics of the region of interest 14 to the THz processing layer 164. Furthermore, The IR sensor layer 160 collects IR radiation from the region of interest 14 and provides a signal IR associated with IR wave characteristics of the region of interest 14 to the IR processing layer 166.

Figure 7:
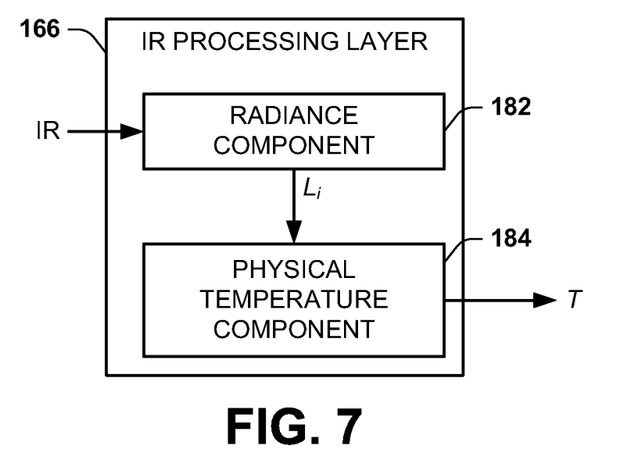
FIG. 7 illustrates an example of an infrared (IR) processing layer in accordance with an aspect of the invention.

FIG. 7 illustrates an example of the IR processing layer 166 in accordance with an aspect of the invention. Reference is to be made to the example of FIG. 6 in the following description of the example of FIG. 7. The IR processing layer 166 includes a radiance component 182 and a physical temperature component 184.

The radiance component 182 receives the signal IR that is provided from the IR sensor layer 160 based on the IR sensor layer 160 collecting the IR radiation from the region of interest 14. As an example, the IR sensor layer 160 can include two thermal IR radiometers operating at two different wavelengths within the wavelength band of approximately 8-14 μm in acquiring the scene radiance $L_i(\theta)$. The scene radiance $L_i(\theta)$ and radiometer radiance $B_i(T)$ acquired by a single radiometer i (i=1, 2) of the two IR respective radiometers could be written as follows:

$$L_i(\theta) = \varepsilon(\theta, ir)B_i(T) + (1 - \varepsilon(\theta, ir))I_{sky}(\theta)$$

Equations 20

-continued $$B_i(T) = \frac{A}{\lambda_i^5 [\exp(B/\lambda_i T) - 1]}$$

Where:
∈(θ, ir) is a scene IR emissivity;
$I_{sky}(\theta)$ is a downward sky radiance;
$B_i(T)$ is a radiometer radiance;
A=1.19104×10$^8$ W μm$^4$ m$^{-2}$ sr$^{-1}$; and
B=14387.7 μmK.

In Equations 20, the scene IR emissivity ∈(θ,ir) can be constant within a selected IR wavelength band. Furthermore, the downward sky radiance $I_{sky}(\theta)$ can be intercepted by a surface of the region of interest 14 and reflected toward the IR sensor layer 160. The radiometer radiance $B_i(T)$ would be measured if a surface of the region of interest 14 was a black body. Thus, each of the IR radiometers of the IR sensor layer 160 can be directed toward the region of interest 14 to acquire the scene radiance $L_i(\theta)$ at the respective wavelength. Therefore, the two measured scene radiance values $L_i(\theta)$ at each wavelength can be provided to the physical temperature component 184.

The physical temperature unit 184 can exploit the two scene radiance values $L_i(\theta)$ provided by the radiance component 182 to calculate the scene physical temperature T, as follows:

$$T \approx \frac{B(\lambda_1 - \lambda_2)}{\lambda_1 \lambda_2 \left[5 \ln\left(\frac{\lambda_1}{\lambda_2}\right) + \ln\left(\frac{L_1(\theta)}{L_2(\theta)}\right)\right]} \quad \text{Equation 21}$$

Because IR emissivity is very high, and because the downward sky radiation has substantially lower values with respect to the equivalent black body radiance, the downward sky radiance $I_{sky}(\theta)$ can be ignored in Equations 20. Therefore, Equation 21 can be rewritten as:

$$L_i(\theta)) \approx \in(\theta,ir) B_i(T) \quad \text{Equation 22}$$

Setting i=1, i=2 in Equation 22, Equation 22 can be rewritten as:

$$L_1(\theta) \approx \in(\theta,ir) B_1(T)$$

$$L_2(\theta) \approx \in(\theta,ir) B_2(T) \quad \text{Equations 23}$$

Dividing Equations 23 and substituting Equations 20 results in the following expression:

$$\frac{L_1(\theta)}{L_2(\theta)} = \left(\frac{\lambda_2}{\lambda_1}\right)^5 \exp\left(\frac{B}{T}\left[\frac{1}{\lambda_2} - \frac{1}{\lambda_1}\right]\right) \frac{1 - \exp(-B/T\lambda_2)}{1 - \exp(-B/T\lambda_1)} \quad \text{Equations 24}$$

$$\frac{L_1(\theta)}{L_2(\theta)} \approx \left(\frac{\lambda_2}{\lambda_1}\right)^4 \exp\left(\frac{B}{T}\left[\frac{1}{\lambda_2} - \frac{1}{\lambda_1}\right]\right) \frac{1 - B/(2T\lambda_2)}{1 - B/(2T\lambda_1)}$$

Taking a natural algorithm of Equations 24 and ignoring terms of higher orders can thus provide the scene physical temperature algorithm of Equation 19. Accordingly, the IR processing layer 166 can calculate the scene physical temperature T and provide it to the MMW processing layer 162 and the THz processing layer 164 for detection of the material 16 and identification of the specific type of material 16.

Figure 8:
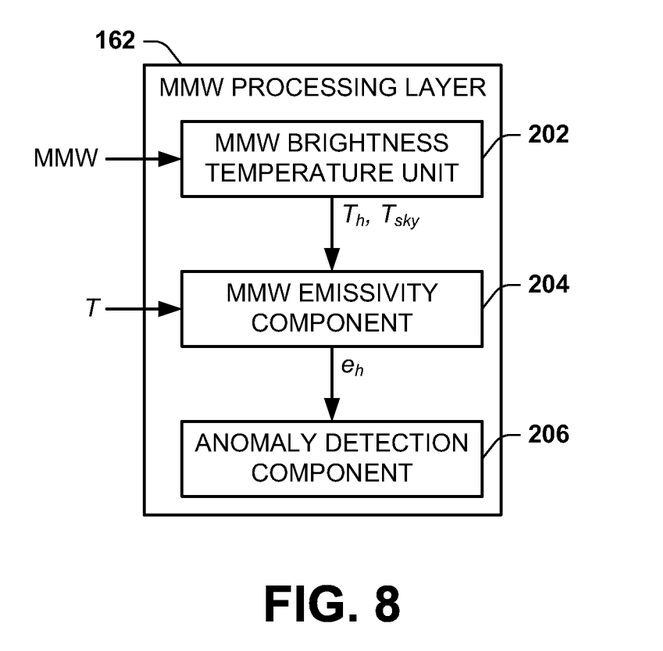
FIG. 8 illustrates an example of a millimeter-wave (MMW) processing layer in accordance with an aspect of the invention.
Figure 9:
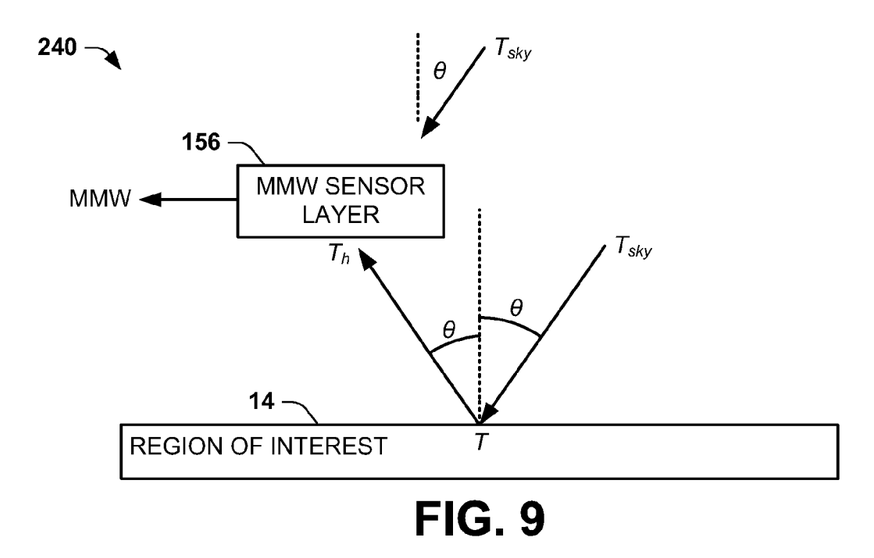
FIG. 9 illustrates an example diagram of collecting MMW radiation in accordance with an aspect of the invention.

FIG. 8 illustrates an example of the MMW processing layer 162 in accordance with an aspect of the invention, and FIG. 9 illustrates an example diagram 240 of collecting MMW radiation in accordance with an aspect of the invention. Reference is to be made to the example of FIG. 6 in the following description of the examples of FIGS. 8 and 9. The MMW processing layer 162 can be configured to measure horizontally-polarized emissivity of the region of interest 14 at a single frequency within an MMW atmospheric window via the MMW sensor layer 156. For example, the MMW atmospheric window can be either approximately 35 GHz or approximately 95 GHz. The MMW processing layer 162 can then identify an observed emissivity anomaly based on the received MMW radiation via the signal MMW. In the example of FIG. 8, the MMW processing layer 162 includes an MMW brightness temperature unit 202, an MMW emissivity component 204, and an anomaly detection component 206.

The MMW processing layer 162 receives the MMW signal data from the MMW sensor layer 156 and at a single frequency f to receive the scene brightness temperature $T_h(\theta, f)$ at an observation angle θ and a sky brightness temperature $T_{sky}(\theta, f)$. As an example, the MMW sensor layer 156 has the capability of rotating around a horizontal axis to measure both the scene brightness temperature $T_h(\theta, f)$ and sky brightness temperature $T_{sky}(\theta, f)$. The scene brightness temperature $T_h(\theta, f)$ at the observation angle θ, acquired by the MMW brightness temperature unit 202 via the signal MMW, can be expressed as follows:

$$T_h(\theta,f) = e_h(\theta,f) T + [1 - e_h(\theta,f)] T_{sky}(\theta,f)$$

$$e_h(\theta,f) = 1 - R_h(\theta,f) \quad \text{Equations 25}$$

Where: T is the scene physical temperature; and
$e_h(\theta, f)$ is the scene emissivity which is related to the scene Fresnel reflectivity $R_h(\theta, f)$.

For measuring sky brightness temperature $T_{sky}(\theta, f)$, the MMW sensor layer 156 can be directed toward the sky with an angle similar to the specular direction of the observation angle θ. The MMW brightness temperature unit 202 can thus calculate the sky brightness temperature $T_{sky}(\theta, f)$ based on the response of the MMW sensor layer 156, as indicated by the signal MMW. Upon obtaining the scene brightness temperature $T_h(\theta, f)$ and the sky brightness temperature $T_{sky}(\theta, f)$, the MMW brightness temperature unit 202 provides the scene brightness temperature $T_h(\theta, f)$ and the sky brightness temperature $T_{sky}(\theta, f)$ to the MMW emissivity component 204.

The MMW emissivity component 204 receives the MMW brightness temperature $T_h(\theta, f)$ and the sky temperature $T_{sky}(\theta, f)$ from the MMW brightness temperature unit 202 and receives the scene physical temperature T from the IR processing layer 166, as described in the example of FIG. 7. Upon obtaining the three temperature values $T_h(\theta, f)$, $T_{sky}(\theta, f)$, and T, the MMW emissivity component 204 can infer $e_h$ a scene emissivity $e_h(\theta, f)$, as derived from Equations 25, as follows:

$$e_h(\theta, f) = \frac{T_h(\theta, f) - T_{sky}(\theta, f)}{T - T_{sky}(\theta, f)} \quad \text{Equation 26}$$

The scene emissivity $e_h(\theta, f)$ is thus provided by the MMW emissivity component 204 to the anomaly detection component 206.

The anomaly detection component 206 detects anomalies within the scene emissivity $e_e(\theta, f)$ of the region of interest 14. At greater observation angles θ (e.g., greater than 40°), such as associated with longer standoff distances, horizontally polarized emissivity can be more sensitive to variations in the region of interest 14 than vertically polarized emissivity. Such sensitivity renders horizontally polarized emissivity better capable of detecting the presence of an anomaly that may correspond to an explosive material than a vertically polarized emissivity. Upon the anomaly detection component 206 determining the presence of an anomaly in the scene emissivity $e_e(\theta, f)$ of the region of interest 14, the material detection system 150 can implement the THz processing layer 164 to determine if the anomaly corresponds to an explosive material.

Figure 10:
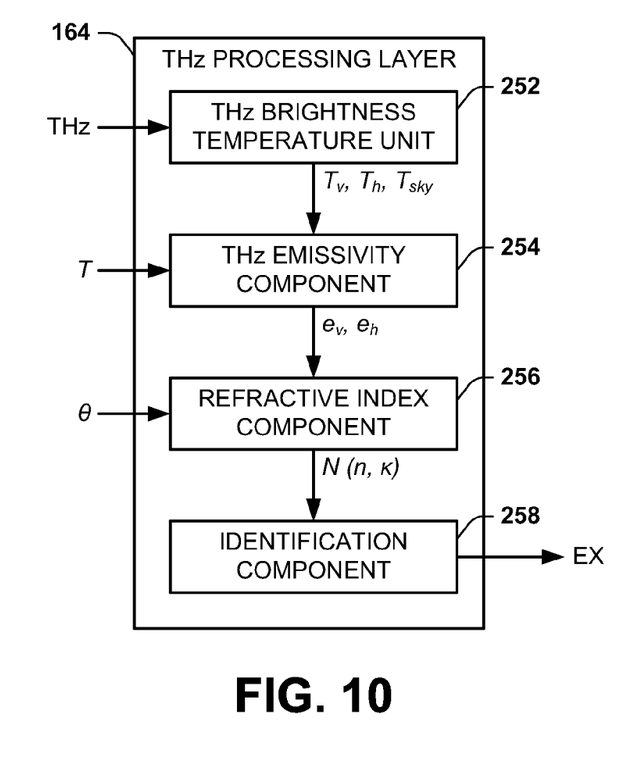
FIG. 10 illustrates an example of a terahertz (THz) processing layer in accordance with an aspect of the invention.

FIG. 10 illustrates an example of a THz processing layer 164 in accordance with an aspect of the invention. Reference is to be made to the example of FIG. 6 in the following description of the example of FIG. 10. The THz processing layer 164 includes a THz brightness temperature unit 252, a THz emissivity component 254, a refractive index component 256, and an identification component 258.

The THz brightness temperature component 252 can receive the signal THz corresponding to THz radiation collected by the THz sensor layer 158. The THz signal can be a single-frequency dual-polarized THz signal operating within either the atmospheric window around 0.22 THz or around 0.65 THz. As an example, these two atmospheric windows may be selected based on a lack of population by any explosive spectral absorption lines, but they can be inhabited by residues of such spectral lines. For example, the two atmospheric windows of around 0.22 THz and around 0.65 THz are located at frequencies below center frequencies of explosive spectral absorption lines, which thus renders explosive materials distinguishable from other non-polar dielectric materials, such as paper, wood, cloth, ceramic, or other dielectric materials. This is because, at these two THz atmospheric windows, the refractivity (i.e., the real portion of the refractive index) of explosive materials may have higher values than such other dielectric materials. The refractivity of an explosive material, such as associated with the center frequency of an absorption spectral line, is an odd function having positive values at frequencies below the center frequency. Since the frequencies within the two atmospheric windows (i.e., approximately 0.22 THz or approximately 0.65 THz) are below all center frequencies of explosive spectral lines, refractivity associated with residues of all absorption spectral lines can be summed within these two windows, thus leading to the higher refractivity values.

The THz brightness temperature unit 252 measures horizontal brightness temperature $T_h(\theta)$, and vertical brightness temperature $T_v(\theta)$ of the region of interest 14 based on the collected THz radiation, as indicated by the signal THz. Similar to the manner of measurement described above regarding the MMW processing layer 162, the THz sensor layer 158 can measure the sky brightness temperature $T_{sky}(\theta, f)$, such as by directing the THz sensor layer 158 toward the sky with an angle similar to the specular direction of the observation angle $\theta$. The THz brightness temperature unit 252 thus provides the two polarized brightness temperature values $T_h(\theta)$, $T_v(\theta)$ and sky brightness temperature $T_{sky}(\theta, f)$ to the THz emissivity component 254.

The THz emissivity component 254 receives the scene brightness temperatures $T_h(\theta)$, $T_v(\theta)$ from the THz brightness temperature unit 252 and receives the scene physical temperature T from the IR processing layer 166, as described in the example of FIG. 7. Upon obtaining the temperature values $T_h(\theta)$, $T_v(\theta)$, $T_{sky}(\theta, f)$, and T, the THz emissivity component 254 can infer a horizontal scene emissivity $e_h(\theta, f)$, as derived from Equation 26 above in a manner similar to as described above regarding the MMW emissivity component 204. The THz emissivity component 254 can also infer a vertical scene emissivity $e_v(\theta, f)$ based on Equations 25 as follows:

$$e_v(\theta, f) = \frac{T_v - T_{sky}(\theta, f)}{T - T_{sky}(\theta, f)} \qquad \text{Equation 27}$$

The two polarized emissivity values $e_h(\theta, f)$, $e_v(\theta, f)$ are then provided to the refractive index component 256.

The refractive index component 256 employs a retrieval algorithm in obtaining the two components of the refractive index N, refractivity n and loss factor $\kappa$, from the THz polarized emissivity values, as follows:

$$N = n - j\kappa \qquad \text{Equation 28}$$

Where: j is the complex number ($j = \sqrt{-1}$).

The algorithm first calculates two variables $P(f, \theta)$ and $Q(f, \theta)$ from the two polarized emissivity values $e_h(\theta, f)$, $e_v(\theta, f)$ as follows:

$$P(\theta, f) = \frac{e_v(\theta, f) - e_h(\theta, f)}{2 - [e_v(\theta, f) + e_h(\theta, f)]} \qquad \text{Equations 29}$$

$$Q(\theta, f) = \frac{e_h(\theta, f)}{2 - e_h(\theta, f)}$$

The variables $P(f, \theta)$ and $Q(f, \theta)$ and the observation angle $\theta$ are then implemented to obtain the real part of the complex cosine of the refraction angle $\beta(\theta, f)$, as follows:

$$\beta(\theta, f) = \frac{P(\theta, f)Q(f, \theta)}{2\cos\theta} \frac{\cos^2\theta - \sin^2\theta}{P(f, \theta)\cos^2\theta - Q(f, \theta)\sin^2\theta} \qquad \text{Equation 30}$$

The complex cosine $\beta(\theta, f)$ is the cosine of the refracted angle inside the explosive material 16. Upon obtaining the real part of the complex cosine $\beta(\theta, f)$, it could be used in obtaining the imaginary part $\alpha(\theta, f)$, as follows:

$$\alpha(\theta, f) = \sqrt{\frac{2\beta(\theta, f)\cos\theta}{Q(\theta, f)} - (\cos^2\theta + \beta^2(\theta, f))} \qquad \text{Equation 31}$$

The refractive index component 256 proceeds in obtaining the real part $\in'(f)$ and the imaginary $\in''(f)$ part of the relative dielectric constant $\in (\in = \in' - j\in'')$, as follows:

$$\in'(f) = \beta^2(\theta, f) - \alpha^2(\theta, f) + \sin^2\theta$$

$$\in''(f) = \beta(\theta, f)\alpha(f, \theta) \qquad \text{Equations 32}$$

The real and imaginary parts $\in'(f), \in''(f)$ of the relative dielectric constant $\in$ depend only on frequency. Therefore, the dependence on the observation angle $\theta$ is canceled in Equations 32. Furthermore, obtaining the relative dielectric constant $\in$ provides the refractive index component 256 with the capability of obtaining the refractive index $N (N = \sqrt{\in})$ and the refractivity n and the loss factor $\kappa$ (i.e., components of the refractive index N) as follows:

$$n = \sqrt{0.5\left(\sqrt{\varepsilon'^2 + \varepsilon''^2} - \varepsilon'\right)} \qquad \text{Equations 33}$$

-continued $$\kappa = \sqrt{0.5\left(\sqrt{\varepsilon'^2 + \varepsilon''^2} - \varepsilon'\right)}$$

After extracting the refractive index N and associated components n, κ of the detected anomaly based on Equations 32 and 33, the identification component 258 can identify the anomaly corresponding to the explosive material 16. This can be achieved through comparing the refractive index N against known values of refractive indices of explosives stored in a database 170 in the example of FIG. 6. If the refractive index value N matches a value within the database 170, the identification component 258 can provide the name of the explosive material 16 associated with that value to a display 168 via a signal EX. Otherwise the identification component 258 can provide an indication to the display 168 that the anomaly corresponding to the explosive material 16 is unknown.

It is to be understood that, in the examples of FIGS. 7, 8, and 10, the IR processing layer 166, the THz processing layer 164, and the MMW processing layer 162 can be configured in a variety of ways. As an example, the MMW brightness temperature unit 202, the THz brightness temperature unit 252, and the radiance component 182 of the respective MMW processing layer 162, THz processing layer 164, and IR processing layer 166 can instead be implemented in the sensor system 152. Thus, the MMW brightness temperature unit 202 can be implemented as part of the MMW sensor layer 156, the THz brightness temperature unit 252 can be implemented as part of the THz sensor layer 158, and the radiance component 182 can be implemented as part of the IR sensor layer 160. Thus, the MMW processing layer 162, the THz processing layer 164, and the IR processing layer 166 can be configured in a variety of ways.

Accordingly, the examples of FIGS. 6-10 demonstrate a manner in which a potentially dangerous material, such as an explosive, can be detected and/or identified based on using a sensor that implements multiple wavelengths. Specifically, the IR sensor layer 160 are implemented to determine the physical temperature of the region of interest 14, the MMW sensor layer 156 is implemented to detect the presence of an explosive based on the physical temperature, and the THz sensor layer 158 is implemented to identify the explosive based on the physical temperature. As a result, the material detection system 150 can be used in a variety of security, military, and/or peacekeeping applications for detecting explosives from sufficiently safe standoff distances.

Figure 11:
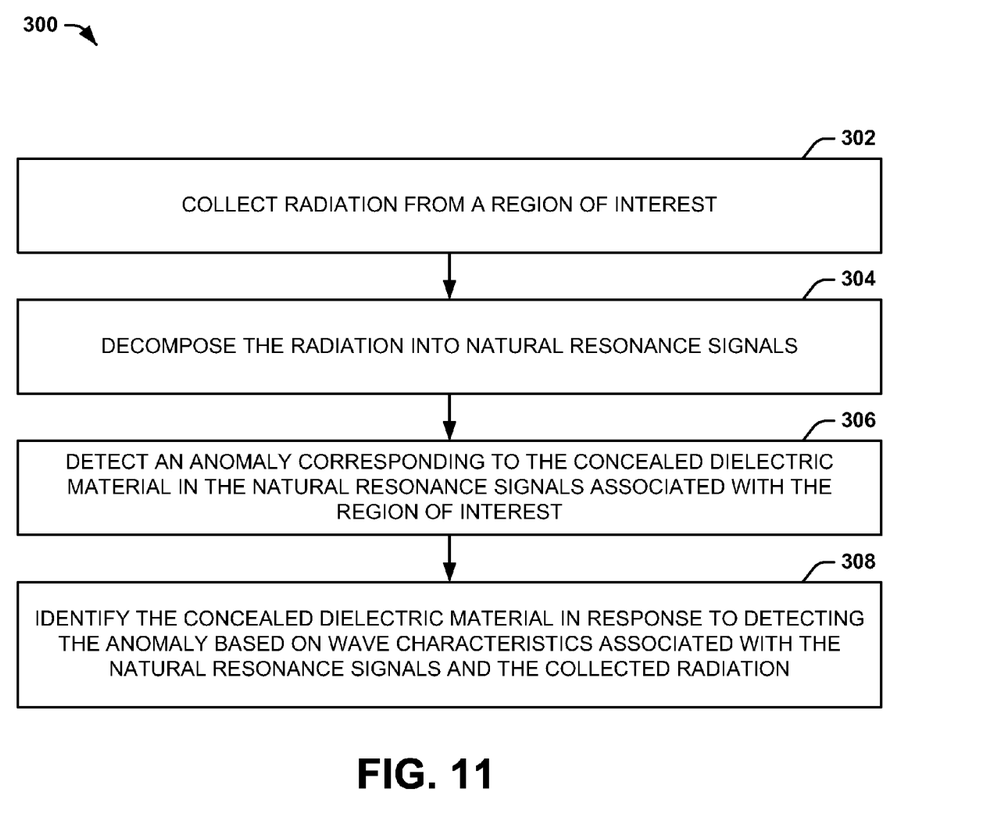
FIG. 11 illustrates an example of a method for detecting and identifying a concealed dielectric material in a region of interest in accordance with an aspect of the invention.
Figure 12:
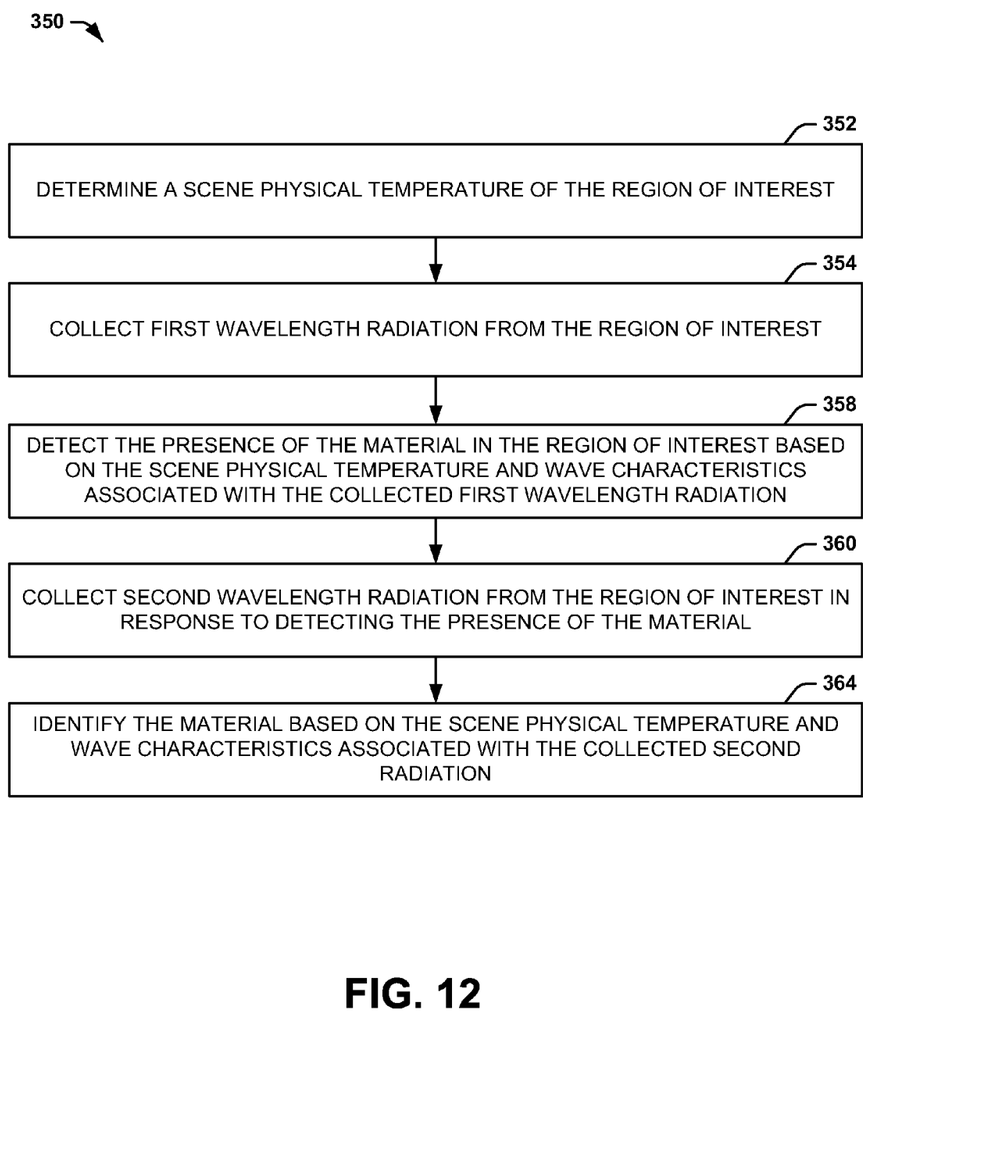
FIG. 12 illustrates an example of method for detecting and identifying a material in a region of interest in accordance with an aspect of the invention.

In view of the foregoing structural and functional features described above, methodologies in accordance with various aspects of the present invention will be better appreciated with reference to FIGS. 11 and 12. While, for purposes of simplicity of explanation, the methodologies of FIGS. 11 and 12 are shown and described as executing serially, it is to be understood and appreciated that the present inventions are not limited by the illustrated order, as some aspects could, in accordance with the present inventions, occur in different orders and/or concurrently with other aspects from that shown and described herein. Moreover, not all illustrated features may be required to implement a given methodology in accordance with aspects of the present inventions.

FIG. 11 illustrates an example of a method 300 for detecting and identifying a concealed dielectric material in a region of interest in accordance with an aspect of the invention. At 302, radiation is collected from the region of interest. The collection of the radiation can be via a sensor that can be implemented as a radiometer or a scatterometer/radar. At 304, the collected radiation is decomposed into natural resonance signals. The decomposition can occur in a natural resonance unit via a total square matrix pencil method (TLS-MPM). At 306, an anomaly corresponding to the concealed dielectric material is detected in the natural resonance signals associated with the region of interest. The identification of the anomaly can occur based on a processing unit analyzing the natural resonance signal data to determine a quantity of poles. At 308, the concealed dielectric material is identified in response to detecting the anomaly based on wave characteristics associated with the natural resonance signals and the collected radiation. The processing unit can be configured to calculate at least one dielectric constant associated with the dielectric material and compare it with dielectric constant data stored in a database.

FIG. 12 illustrates an example of a method 350 for detecting and identifying a material in a region of interest in accordance with an aspect of the invention. At 352, a scene physical temperature of the region of interest is determined. The physical temperature can be determined based on an IR radiometer. At 354, first wavelength radiation is collected from the region of interest. The first wavelength radiation can be MMW radiation. At 356, the presence of the material is detected in the region of interest based on the scene physical temperature and wave characteristics associated with the collected first wavelength radiation. The wave characteristics can include emissivity data associated with the region of interest calculated based on the collected first wavelength radiation and the physical temperature of the region of interest. The calculation of the emissivity value can be performed by a processing unit implementing a mathematical algorithm. A detected anomaly in the emissivity data can be indicative of the presence of the material. At 358, second wavelength radiation is collected from the region of interest in response to detecting the presence of the material. The second wavelength radiation can be THz radiation. At 360, the material is identified based on the scene physical temperature and wave characteristics associated with the collected second wavelength radiation. The identification can be based on calculating a refractive index of the material based on the collected second wavelength radiation and a physical temperature of the material. The identification can be based on a comparison of known refractive indices in a database.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A material detection system comprising:
a sensor system configured to collect radiation from a region of interest; and
a processing unit configured to decompose the collected radiation into natural resonance signals, to analyze the natural resonance signals to identify poles and a residue in the natural resonance signals, to implement an algorithm to extract an observation angle of the collected radiation based on characteristics of the poles and the residue in the natural resonance signals, and to detect an anomaly corresponding to a concealed dielectric material based on calculating at least one dielectric constant associated with the concealed dielectric material based on wave characteristics of the natural resonance signals and based on the extracted observation angle, and to identify the dielectric material by comparing the at least one dielectric constant with dielectric constant data stored in a database.

2. The method of claim 1, wherein the sensor system is configured to collect orthogonally-polarized terahertz (THz) signals from the region of interest.

3. The system of claim 1, wherein the processing unit is configured to detect the anomaly based on a quantity of the poles in the natural resonance signals.

4. The system of claim 1, wherein the processing unit is further configured to estimate characteristics associated with at least one intervening material that conceals the concealed dielectric material based on the extracted observation angle, extract Fresnel reflection coefficients associated with interfaces between atmosphere and the at least one intervening material and between the at least one intervening material and the concealed dielectric material based on the characteristics of the at least one intervening material and the extracted observation angle, and to calculate the at least one dielectric constant associated with the concealed dielectric material based on the extracted observation angle, the estimated characteristics associated with at least one intervening material, and the extracted Fresnel reflection coefficients.

5. The system of claim 1, wherein the at least one dielectric constant comprises real and imaginary portion operators calculated based on the wave characteristics of the natural resonance signals and wave characteristics of the collected radiation.

6. A method for detecting and identifying a concealed dielectric material in a region of interest, the method comprising:
collecting radiation from the region of interest;
decomposing the collected radiation into natural resonance signals;
implementing an algorithm to extract an observation angle of the collected radiation based on wave characteristics of the natural resonance signals;
estimating a depth and a dielectric constant of at least one intervening material that conceals the concealed dielectric material based on the extracted observation angle;
extracting Fresnel reflection coefficients associated with interfaces between atmosphere and the at least one intervening material and between the at least one intervening material and the concealed dielectric material based on the dielectric constant of the at least one intervening material and the extracted observation angle;
calculating a dielectric constant associated with the concealed dielectric material based on the extracted Fresnel reflection coefficients; and
identifying the concealed dielectric material based on the dielectric constant associated with the concealed dielectric material.

7. The method of claim 6, wherein collecting the radiation comprises collecting orthogonally-polarized terahertz (THz) signals from the region of interest.

8. The method of claim 6, wherein detecting the anomaly comprises counting a quantity of poles in the natural resonance signals.

9. The method of claim 6, wherein identifying the dielectric material comprises comparing the at least one dielectric constant with a dielectric constant data stored in a database.

10. A material detection and identification system comprising:
a sensor system configured to collect radiation comprising a plurality of frequency bands from a region of interest; and
a processing unit comprising:
an infrared (IR) processing layer associated with IR radiation collected by the sensor system, the IR processing layer being configured to determine a scene physical temperature associated with the region of interest;
a first processing layer associated with a first frequency band of the plurality of frequency bands of the radiation, the first processing layer being configured to detect a material of interest in the region of interest based on wave characteristics associated with the first frequency band and the scene physical temperature; and
a second processing layer associated with a second frequency band of the plurality of frequency bands of the radiation, the second processing layer being configured to identify the material of interest based on wave characteristics associated with the second frequency band and the scene physical temperature.

11. The system of claim 10, wherein the first frequency band is associated with millimeter wave (MMW) radiation collected from the region of interest by the sensor system, and wherein the second frequency band is associated with terahertz (THz) radiation collected from the region of interest by the sensor system.

12. The system of claim 10, wherein the first processing layer is configured to calculate emissivity data associated with the region of interest based on the wave characteristics associated with the first frequency band and a physical temperature of the region of interest, the first processing layer being configured to detect the material of interest based on an anomaly associated with the emissivity data.

13. The system of claim 12, wherein the first processing layer is configured to calculate the emissivity data based on brightness temperatures measured based on the first frequency band at a common observation angle associated with the sensor system.

14. The system of claim 10, wherein processing unit further comprises a database configured to store refractive index data associated with a plurality of materials, wherein the second processing layer is configured to calculate a refractive index of the material of interest based on the wave characteristics associated with the second frequency band and a physical temperature of the region of interest, the second processing layer being configured to identify the material of interest based on comparing the refractive index of the material of interest with the refractive index data stored in the database.

15. The system of claim 14, wherein the second processing layer is configured to calculate the refractive index of the material based on orthogonally-polarized brightness temperatures measured based on the second frequency band at an observation angle associated with the sensor system.

16. A method for detecting and identifying a material in a region of interest, the method comprising:
collecting infrared (IR) radiation of the region of interest;
calculating a scene physical temperature based on measured wave characteristics associated with the collected IR radiation of the region of interest;
collecting radiation in a first frequency band from the region of interest;
detecting the presence of the material in the region of interest based on the scene physical temperature and wave characteristics associated with the collected first frequency band radiation;

collecting radiation in a second frequency band from the region of interest in response to detecting the presence of the material; and identifying the material based on the scene physical temperature and wave characteristics associated with the collected second frequency band radiation.

17. The method of claim 16, wherein collecting the first frequency band radiation comprises collecting millimeter-wave (MMW) radiation of the region of interest, and wherein collecting the second frequency band radiation comprises collecting terahertz (THz) radiation of the region of interest.

18. The method of claim 16, wherein detecting the presence of the material in the region of interest comprises:

calculating emissivity data associated with the region of interest based on the wave characteristics associated with the collected first frequency band radiation and the scene physical temperature; and determining an anomaly associated with the emissivity data corresponding to the material.

19. The method of claim 16, wherein identifying the material comprises:

calculating a refractive index of the material of interest based on the wave characteristics associated with the collected second frequency band radiation and the scene physical temperature; and comparing the refractive index of the material with refractive index data stored in a database.

20. The system of claim 10, wherein each of the plurality of frequency bands is at least one order of magnitude different with respect to wavelength than each other one of the plurality of frequency bands.

21. The method of claim 16, wherein each of the first and second frequency bands are at least one order of magnitude different with respect to wavelength relative to each other.

* * * * *